(12) United States Patent
Boling et al.

(10) Patent No.: US 8,880,176 B2
(45) Date of Patent: Nov. 4, 2014

(54) IMPLANTABLE NEURAL STIMULATION ELECTRODE ASSEMBLIES AND METHODS FOR STIMULATING SPINAL NEURAL SITES

(75) Inventors: C. Lance Boling, San Jose, CA (US); Anthony V. Caparso, San Jose, CA (US)

(73) Assignee: Nevro Corporation, Menlo Park, CA (US)

( * ) Notice: Subject to any disclaimer, the term of this patent is extended or adjusted under 35 U.S.C. 154(b) by 941 days.

(21) Appl. No.: 12/468,688

(22) Filed: May 19, 2009

(65) Prior Publication Data

US 2009/0319013 A1    Dec. 24, 2009

Related U.S. Application Data

(60) Provisional application No. 61/054,327, filed on May 19, 2008.

(51) Int. Cl.
  *A61N 1/00* (2006.01)
  *A61N 1/05* (2006.01)
(52) U.S. Cl.
  CPC .................................. *A61N 1/0553* (2013.01)
  USPC .......................................................... 607/45
(58) Field of Classification Search
  None
  See application file for complete search history.

(56) References Cited

U.S. PATENT DOCUMENTS

| | | | |
|---|---|---|---|
| 3,738,368 A | 6/1973 | Avery et al. |
| 4,136,703 A | 1/1979 | Wittkampf |
| 5,042,486 A | 8/1991 | Pfeiler et al. |
| 5,078,140 A | 1/1992 | Kwoh |
| 5,179,962 A | 1/1993 | Dutcher et al. |
| 5,211,165 A | 5/1993 | Dumoulin et al. |
| 5,251,634 A | 10/1993 | Weinberg |
| 5,257,636 A | 11/1993 | White |
| 5,325,873 A | 7/1994 | Hirschi et al. |
| 5,336,182 A | 8/1994 | Lundquist et al. |
| 5,354,326 A | 10/1994 | Comben et al. |
| 5,375,596 A | 12/1994 | Twiss et al. |
| 5,392,791 A | 2/1995 | Nyman |
| 5,425,367 A | 6/1995 | Shapiro et al. |
| 5,480,421 A | 1/1996 | Otten |

(Continued)

OTHER PUBLICATIONS

Partial International Search Report, International Application No. PCT/US2009/044555, Applicant: Nevro Corporation, mailed Aug. 13, 2009, 6 pages, European Patent Office.

(Continued)

*Primary Examiner* — Christopher D Koharski
*Assistant Examiner* — Elizabeth K So
(74) *Attorney, Agent, or Firm* — Perkins Coie LLP

(57) ABSTRACT

An implantable neurostimulation electrode assembly comprises a first electrode unit and a second electrode unit configured to be arranged in a side-by-side configuration. The first electrode unit includes a dielectric first paddle, a plurality of first electrodes carried by the first paddle, and a guideline. The guideline has a distal section affixed to the first paddle and a proximal section having a length configured to extend externally of a patient. The second electrode unit has a dielectric second paddle and a plurality of second electrodes carried by the second paddle. The second paddle is configured to travel along the guideline and contact the first paddle in the side-by-side configuration. As a result, the first and second electrode units of this embodiment can be passed percutaneously through the same percutaneous entry hole and assembled in vivo at the stimulation site to form a larger paddle-type electrode array without surgical implantation.

14 Claims, 9 Drawing Sheets

(56) References Cited

U.S. PATENT DOCUMENTS

| | | |
|---|---|---|
| 5,549,555 A | 8/1996 | Sohn |
| 5,641,326 A | 6/1997 | Adams |
| 5,727,553 A | 3/1998 | Saad |
| 5,728,148 A | 3/1998 | Bostrom et al. |
| 5,733,322 A | 3/1998 | Starkebaum |
| 5,741,319 A | 4/1998 | Woloszko et al. |
| 5,824,030 A | 10/1998 | Yang et al. |
| 5,871,487 A | 2/1999 | Warner et al. |
| 5,871,531 A | 2/1999 | Struble |
| 6,024,702 A | 2/2000 | Iversen |
| 6,066,163 A | 5/2000 | John |
| 6,161,047 A | 12/2000 | King |
| 6,192,278 B1 | 2/2001 | Werner |
| 6,198,963 B1 | 3/2001 | Haim et al. |
| 6,415,187 B1 | 7/2002 | Kuzma et al. |
| 6,474,341 B1 | 11/2002 | Hunter et al. |
| 6,714,822 B2 | 3/2004 | King |
| 6,875,571 B2 | 4/2005 | Crabtree et al. |
| 6,895,283 B2 | 5/2005 | Erickson et al. |
| 6,934,589 B2 | 8/2005 | Sundquist |
| 7,072,719 B2 | 7/2006 | Vinup |
| 7,146,222 B2 | 12/2006 | Boling |
| 7,363,089 B2 | 4/2008 | Vinup et al. |
| 7,379,776 B1 | 5/2008 | Chitre et al. |
| 7,455,666 B2 | 11/2008 | Purdy |
| 7,477,945 B2 | 1/2009 | Rezai et al. |
| 7,590,454 B2 | 9/2009 | Garabedian et al. |
| 7,702,379 B2 | 4/2010 | Avinash et al. |
| 7,769,472 B2 | 8/2010 | Gerber |
| 7,970,480 B2 | 6/2011 | Swanson |
| 7,996,055 B2 | 8/2011 | Hauck et al. |
| 8,019,442 B1 | 9/2011 | Swanson et al. |
| 8,099,172 B2 | 1/2012 | Swanson |
| 8,197,494 B2 | 6/2012 | Jaggi et al. |
| 8,326,439 B2 | 12/2012 | Boling et al. |
| 2002/0128700 A1 | 9/2002 | Cross |
| 2002/0173718 A1 | 11/2002 | Frisch et al. |
| 2003/0114752 A1 | 6/2003 | Henderson et al. |
| 2003/0120150 A1 | 6/2003 | Govari |
| 2003/0125786 A1 | 7/2003 | Gliner et al. |
| 2003/0136418 A1 | 7/2003 | Behm |
| 2004/0097803 A1 | 5/2004 | Panescu |
| 2004/0176683 A1 | 9/2004 | Whitin et al. |
| 2005/0049486 A1 | 3/2005 | Urquhart et al. |
| 2005/0065588 A1 | 3/2005 | Zhao et al. |
| 2005/0075684 A1 | 4/2005 | Phillips et al. |
| 2005/0085884 A1 | 4/2005 | O'Brien et al. |
| 2005/0113882 A1 | 5/2005 | Cameron |
| 2005/0154435 A1 | 7/2005 | Stern et al. |
| 2005/0203599 A1* | 9/2005 | Garabedian et al. .......... 607/116 |
| 2005/0234318 A1 | 10/2005 | Schulman et al. |
| 2005/0251237 A1 | 11/2005 | Kuzma et al. |
| 2006/0089691 A1 | 4/2006 | Kaplan et al. |
| 2006/0161219 A1 | 7/2006 | Mock et al. |
| 2006/0161235 A1 | 7/2006 | King |
| 2007/0073353 A1 | 3/2007 | Rooney et al. |
| 2007/0106289 A1 | 5/2007 | O'Sullivan |
| 2007/0239249 A1 | 10/2007 | Tockman et al. |
| 2007/0249901 A1 | 10/2007 | Ohline et al. |
| 2007/0255364 A1 | 11/2007 | Gerber et al. |
| 2007/0261115 A1 | 11/2007 | Gerber et al. |
| 2007/0276450 A1 | 11/2007 | Meadows et al. |
| 2008/0039738 A1 | 2/2008 | Dinsmoor et al. |
| 2008/0097475 A1 | 4/2008 | Jaggi et al. |
| 2008/0125833 A1 | 5/2008 | Bradley et al. |
| 2008/0183224 A1 | 7/2008 | Barolat |
| 2009/0018630 A1 | 1/2009 | Osypka et al. |
| 2009/0204173 A1 | 8/2009 | Fang et al. |
| 2009/0299444 A1 | 12/2009 | Boling |
| 2010/0069736 A1 | 3/2010 | Finneran et al. |
| 2010/0204569 A1 | 8/2010 | Burnside et al. |
| 2011/0031961 A1 | 2/2011 | Durand et al. |
| 2011/0160568 A1 | 6/2011 | Seeley et al. |
| 2012/0083709 A1 | 4/2012 | Parker et al. |
| 2012/0083856 A1 | 4/2012 | Thacker et al. |
| 2013/0144305 A1 | 6/2013 | Boling et al. |

OTHER PUBLICATIONS

International Search Report and Written Opinion; International Application No. PCT/US2009/044555, Applicant: Nevro Corporation; European Patent Office; mailed Dec. 2, 2009, 18 pages.

\* cited by examiner

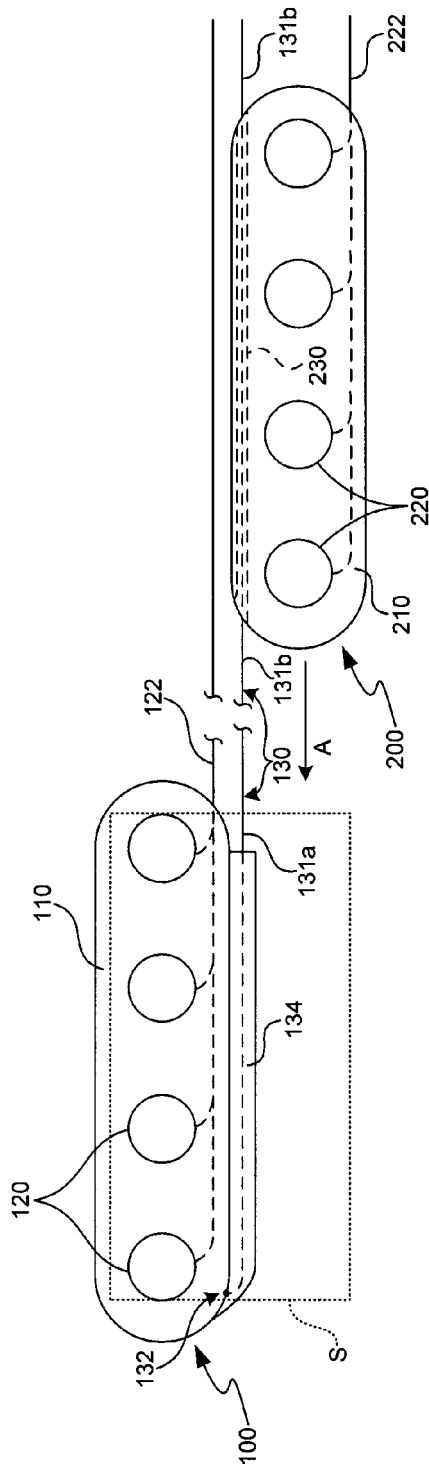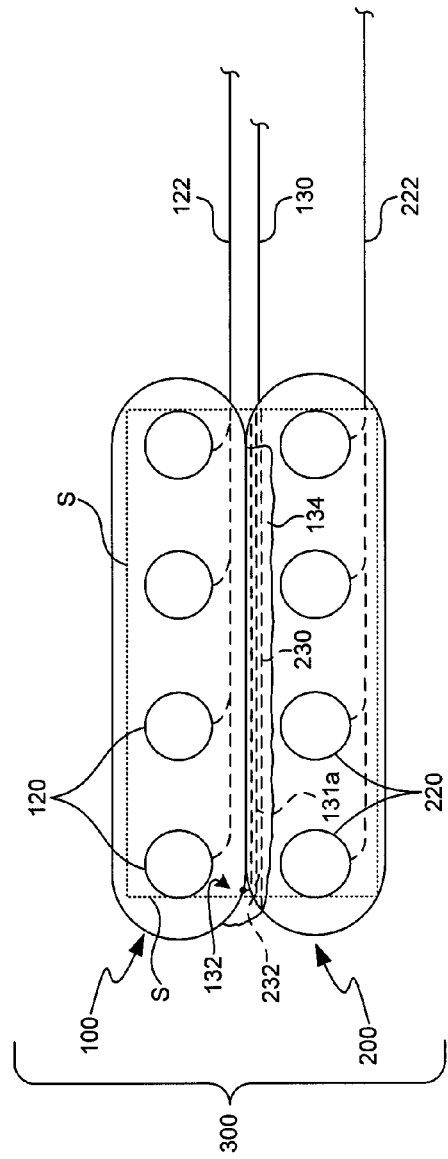

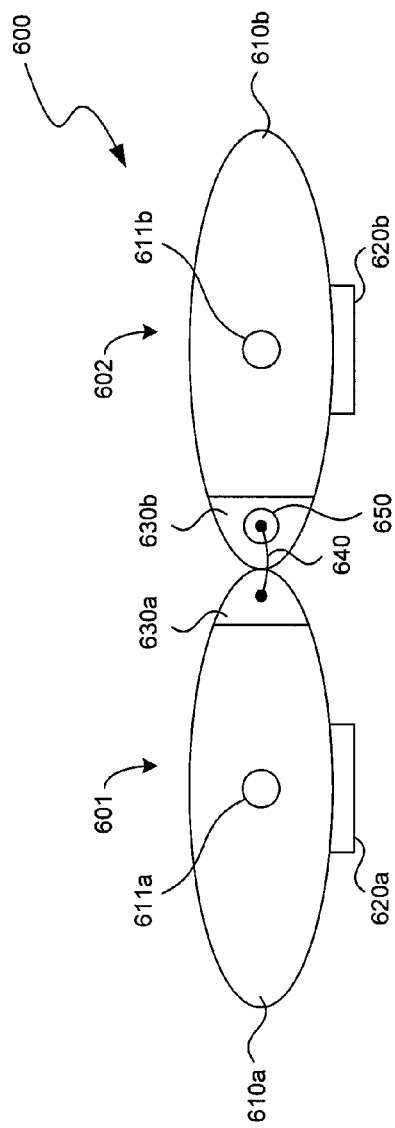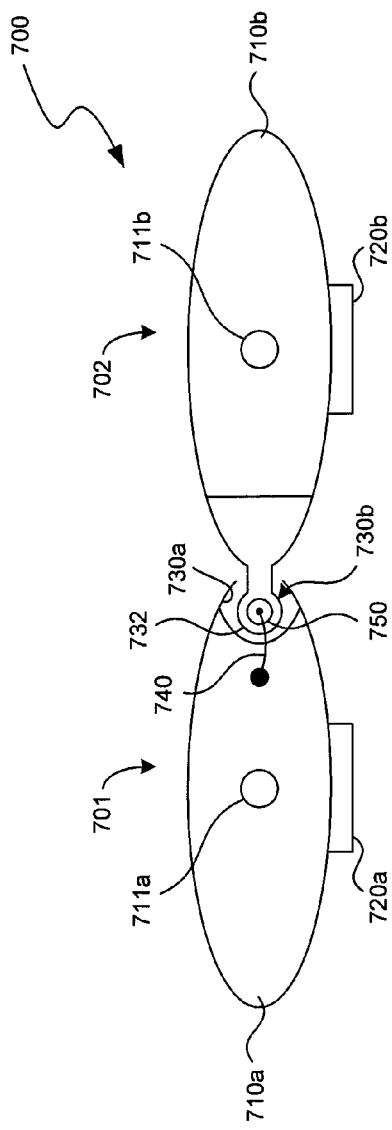

IMPLANTABLE NEURAL STIMULATION ELECTRODE ASSEMBLIES AND METHODS FOR STIMULATING SPINAL NEURAL SITES

CROSS REFERENCE TO RELATED APPLICATION

This application claims the benefit of U.S. Provisional Application No. 61/054,327, entitled "IMPLANTABLE NEURAL STIMULATION ELECTRODES ASSEMBLIES AND METHODS FOR STIMULATING SPINAL NEURAL SITES," filed May 19, 2008, and is hereby incorporated by reference.

TECHNICAL FIELD

The following disclosure relates to implantable neural stimulation electrode assemblies for use in spinal cord stimulation and other neurological applications.

BACKGROUND

Neurological stimulators have been developed to treat pain, movement disorders, functional disorders, spasticity, cancer, cardiac disorders, and several other medical conditions. Implantable neurological stimulation systems generally have an implantable pulse generator and one or more electrode leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings are individual electrodes. In many cases, the SCS leads are implanted percutaneously through a large needle inserted into the epidural space. One concern of cylindrical SCS leads is that they deliver electrical current completely around the lead body because ring-type electrodes typically cover the full circumference of the lead. This is undesirable because the current flow into the areas of the anatomy away from the spinal cord can cause undesirable collateral stimulation. A significant portion of the power is also wasted with cylindrical SCS leads because the energy directed away from the spinal cord does not affect the nerves, but rather it significantly reduces the current density delivered to the target neural tissue. Another challenge of cylindrical leads is that they may migrate after implantation. As such, many cylindrical leads require additional fixation devices to hold the leads at a desired stimulation site.

Another type of stimulation lead is a paddle lead. Paddle leads typically have a relatively flat body with electrodes arranged on one side of the body. Paddle leads are commonly used for cortical stimulation and SCS applications. Large paddle leads are desirable because they cover more neurological structures, but large paddle leads are not well suited for percutaneous implantation. As a result, large paddle leads are often surgically implanted using highly invasive procedures that are costly and can lead to complications. Smaller paddle leads can be percutaneously implanted, but small paddle leads may not be appropriate for many SCS applications. For example, dorsal root SCS applications or other applications may benefit from conventional large electrode arrays that to date have not been implanted percutaneously.

BRIEF DESCRIPTION OF THE DRAWINGS

FIG. 3A is a bottom plan view of first and second electrode assemblies at a stage of a method for implanting an electrode assembly into a patient in accordance with an embodiment of the invention.

FIG. 3B is a bottom plan view of an assembled electrode assembly at a stimulation site within a patient in accordance with an embodiment of the invention.

FIG. 6 is a cross-sectional view illustrating an assembled electrode assembly in accordance with another embodiment of the invention.

FIG. 7 is a cross-sectional view illustrating an assembled electrode assembly in accordance with yet another embodiment of the invention.

DETAILED DESCRIPTION

A. Overview

Figure 1A:
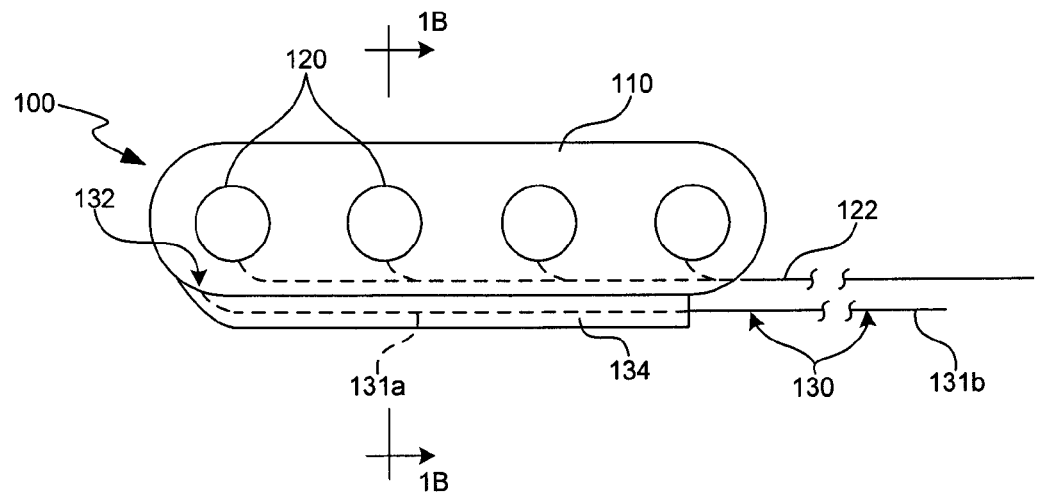
FIG. 1A is a bottom plan view and FIG. 1B is a cross-sectional view taken along line 1B-1B of FIG. 1A of an embodiment of a first electrode unit for an electrode assembly in accordance with an embodiment of the invention.

Specific details of several embodiments of the disclosure are described below with reference to implantable electrode assemblies for stimulating neural structures, methods for implanting neural stimulation electrode assemblies, and methods for stimulating a spinal neural site of a patient. Although selected embodiments are described below with respect to stimulating the dorsal root to control pain, the electrode assemblies may be used for stimulating the brain, peripheral neurological structures, or other tissues (e.g., muscles). Several other embodiments of the invention can have different configurations, components, or procedures than those described in this section. A person of ordinary skill in the art, therefore, will accordingly understand that the invention may have other embodiments with additional elements, or the invention may have other embodiments without several of the features shown and described below with reference to FIGS. 1-10.

One embodiment of an implantable neurostimulation electrode assembly comprises a first electrode unit and a second electrode unit configured to be arranged in a side-by-side configuration. The first electrode unit includes a dielectric first paddle, a plurality of first electrodes carried by the first paddle, and a guideline. The guideline has a distal section affixed to the first paddle and a proximal section having a length configured to extend externally of a patient. The second electrode unit has a dielectric second paddle and a plurality of second electrodes carried by the second paddle. The second paddle is configured to travel along the guideline and contact the first paddle in the side-by-side configuration. As a result, the first and second electrode units of this embodiment can be passed percutaneously through the same percutaneous entry hole and assembled in vivo at the stimulation site to form a larger paddle-type electrode array without surgical implantation.

Another embodiment of an implantable neural stimulation electrode assembly comprises a first electrode unit having a dielectric first paddle, first electrodes carried by the first paddle, and a first electrical line connected to at least one of the first electrodes. The first electrode unit further includes a guideline having a distal section attached to the first paddle and a proximal section extending proximally of the first paddle. The implantable neural stimulation electrode assembly of this embodiment also includes a second electrode unit having a dielectric second paddle, a lumen through the second paddle, and second electrodes carried by the second paddle. The lumen through the second paddle is configured to receive and slide along the guideline such that the second electrode unit is positioned adjacent to the first electrode unit when the second electrode until is at the distal section of the guideline.

A further embodiment of an implantable neural stimulation electrode assembly comprises a first electrode unit having a dielectric first support with a first contact surface and a first back surface. The first electrode unit further includes a plurality of first electrodes at the first contact surface such that the first electrodes are electrically isolated from the first back surface. The electrode assembly also includes a second electrode unit having a dielectric second support with a second contact surface and a second back surface. The first and second dielectric supports are separate components that can slide relative to each other. The second electrode unit further includes a plurality of second electrodes at the second contact surface of the second support such that the second electrodes are electrically isolated from the second back surface of the second support. The second support is configured to directly engage the first support in vivo such that the first contact surface and the second contact surface face in common direction.

An embodiment of a method of implanting a neural stimulation electrode assembly at a spinal cord of a patient comprises percutaneously placing a distal portion of a cannula into the epidural space at the spine of the patient, and advancing a first electrode unit through the cannula and into the epidural space. The first electrode unit has a guideline fixed to a portion of the first electrode unit, and the guideline extends through the cannula. The method can further include sliding a second electrode unit over the guideline and into the epidural space such that the second electrode unit directly contacts the first electrode unit.

An embodiment of a method for stimulating a spinal neural site of a patient comprises percutaneously placing a distal portion of a cannula into the patient and advancing a first electrode unit through the cannula and into an epidural space at the spine of the patient. The first electrode unit has a guideline fixed to a portion of the first electrode unit, and the guideline extends through the cannula. This method further includes sliding a second electrode unit along the guideline and into the epidural space such that the second electrode unit directly contacts the first electrode unit. After sliding the second electrode unit directly into contact with the first electrode unit, the method includes delivering an electrical signal to the patient via at least one of the first and second electrode units.

B. Embodiments of Implantable Neural Stimulation Electrode Assemblies

Figure 1B:
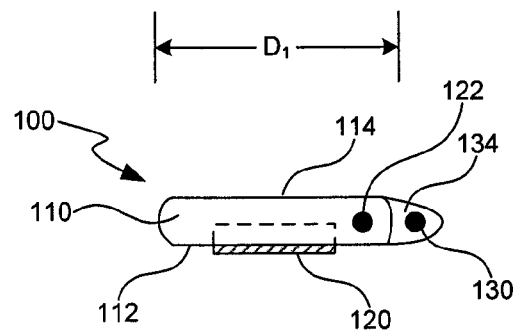

FIG. 1A is a bottom view of an embodiment of a first electrode unit 100 and FIG. 1B is a cross-sectional view taken along line 1B-1B of FIG. 1A. In this embodiment, the first electrode unit includes a dielectric first support 110 and at least one first electrode 120 carried by the first support 110. Referring to FIG. 1B, the first support 110 can be a paddle having a first contact surface 112, a back surface 114, and a first cross-sectional dimension D, greater than a second cross-sectional dimension $D_2$. Referring to FIGS. 1A and 1B together, the illustrated embodiment of the electrode unit 100 includes a plurality of first electrodes 120 at the first contact surface 112 that are electrically isolated from the back surface 114. The first electrodes 120 can project beyond the first contact surface 112 (FIG. 1B), but in other embodiments the first electrodes 120 can be flush or recessed relative to the first contact surface 112. The first support 110 can be made from a flexible bio-compatible material, such as silicone, and the first electrodes 120 can be made from stainless steel, titanium, or another electrically conductive bio-compatible material. The first electrodes 120 are electrically coupled to at least one first electrical line 122 that has a proximal section configured to be coupled to an implantable pulse generator and a distal section on and/or in the first support 110. The first electrodes 120 shown in FIG. 1A are all coupled to a single first electrical line 122 such that the first electrodes 120 are biased at a common potential. In alternative embodiments, individual first electrodes 120 can be coupled to independent electrical lines such that the first electrodes 120 can be biased independently at different potentials and/or polarities.

The first electrode unit 100 further includes a guideline 130 having a distal section 131a and a proximal section 131b. The distal section 131a has an end 132 fixed to the first support 110, and the proximal section 131b has a length configured to extend externally of the patient. The first electrode unit 100 can further include a casing 134 around a portion of the distal section 131a of the guideline 130. The casing 134 can be formed integrally with the first support 110, or the casing 134 can be a separate element attached to the first support 110. In the embodiment illustrated in FIGS. 1A and 1B, the casing 134 is a soft, deformable silicone strip formed along an edge of the first support 110 to securely retain a portion of the distal section 131a of the guideline 130 next to the side of the first support 110. As best shown in FIG. 1B, the casing 134 can have a perforated edge 135 that allows the casing 134 to split open as described below.

Figure 2A:
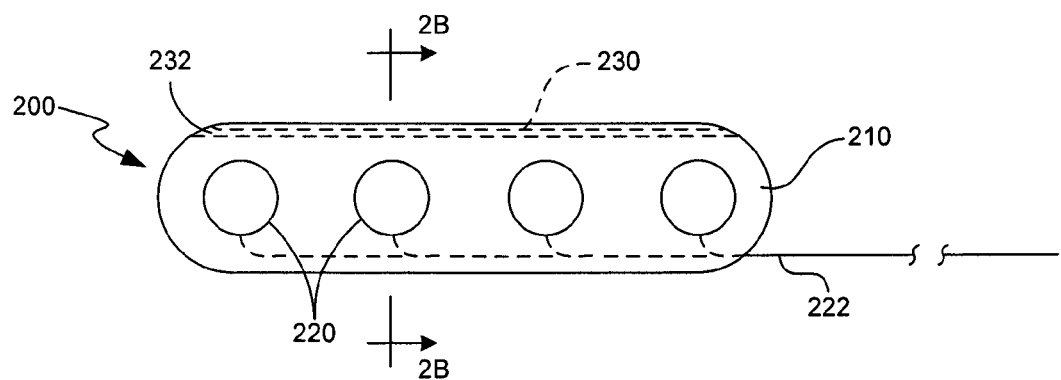
FIG. 2A is a bottom plan view and FIG. 2B is a cross-sectional view taken along line 2B-2B of FIG. 2A of an embodiment of a second electrode unit for the electrode assembly in accordance with an embodiment of the invention.
Figure 2B:
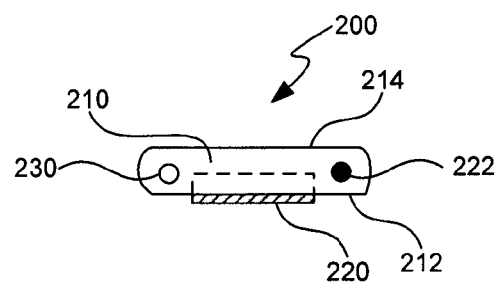

FIG. 2A is a bottom view of an embodiment of a second electrode unit 200 for use in conjunction with the first electrode unit 100, and FIG. 2B is a cross-sectional view taken along line 2B-2B. In this embodiment, the second electrode unit 200 includes a second dielectric support 210, a plurality of second electrodes 220 carried by the second dielectric support 210, and a second electrical line 222 electrically coupled to the second electrodes 220. Referring to FIG. 2B, the second support 210 can have a second contact surface 212 at which the second electrodes 220 are exposed and a back surface 214 electrically isolated from the second electrodes 220. The second electrodes 220 can be commonly coupled to a single second electrical line 222 as shown in FIG. 2B, or alternatively the second electrodes 220 can be electrically coupled to independent second electrical lines to operate at different potentials and/or polarities. The second support 210, second electrodes 220, and second electrical line 222 can be the same as or similar to the corresponding components of the first electrode unit 100 described above with reference to FIGS. 1A and 1B. The second electrode unit 200 is different than the first electrode unit 100 in that the second electrode unit 200 includes a lumen 230 configured to receive and slide along the guideline 130 of the first electrode unit 100. The lumen 230 can have a flared distal aperture 232 that opens laterally to provide a larger orifice to accommodate the end 132 of the distal section 131a of the guideline 130. As explained in more detail below, the second electrode unit 200 travels along the guideline 130 of the first electrode unit 100 until it is adjacent to the first support 100 in a side-by-side configuration within a patient.

FIG. 3A illustrates a stage of percutaneously implanting and assembling a stimulation electrode assembly in vivo at a stimulation site S (shown in dotted lines) within a patient. At this stage, the first electrode unit 100 has been percutaneously implanted through a needle, cannula, trocar, catheter, or other suitable percutaneous implanters using known guidance systems to be positioned at the stimulation. site S. For example, the first electrode unit 100 can be implanted into the epidural space of the spine by inserting a needle through the flavum ligament and into the epidural space and then advancing the first electrode unit 100 into the epidural space via the needle. The first electrical line 122 and the guideline 130 can extend through the patient and the needle such that the proximal section of the first electrical line 122 and the proximal section 131b of the guideline 130 are accessible externally of the patient. The second electrode unit 200 can then be advanced over the guideline 130 and into the patient (arrow A) by inserting the proximal section 131b of the guideline 130 into the lumen 230 of the second electrode unit 200. The second electrode unit 200 can be advanced through the needle, or in other embodiments the needle can be removed from the patient and the second electrode unit 200 can be advanced along the guideline 130 through the percutaneous opening and pathway through the patient created by the needle.

FIG. 3B illustrates a subsequent stage of a method for implanting the first and second electrode units 100 and 200 to assemble a neural stimulation electrode assembly 300 at the stimulation site S within the patient. To reach this stage of the method, the second electrode unit 200 is advanced along the guideline 130 as shown in FIG. 3A until the distal section 131a is received in the lumen 230 and the aperture 232 of the lumen 230 is proximate to the end 132 of the guideline 130. As the second electrode unit 200 advances along the distal section 131a of the guideline 130, the second electrode unit 200 can split the casing 134 along the edge 235. The second electrode unit 200 is accordingly adjacent to the first electrode unit 100 in a side-by-side configuration within the patient when the second electrode unit 200 is at the distal section 131a of the guideline 130. The second electrode unit 200 can in fact contact or otherwise engage the first electrode unit 100 when the second electrode unit 200 is at the distal section 131a of the guideline 130. In this embodiment, the casing 134 is a soft material that splits apart as the second electrode unit 200 advances along the distal section 131a of the guideline 130. The casing 134 can accordingly grip the second electrode unit 200 to inhibit the second electrode unit 200 from moving away from the first electrode unit 100.

Figure 4:
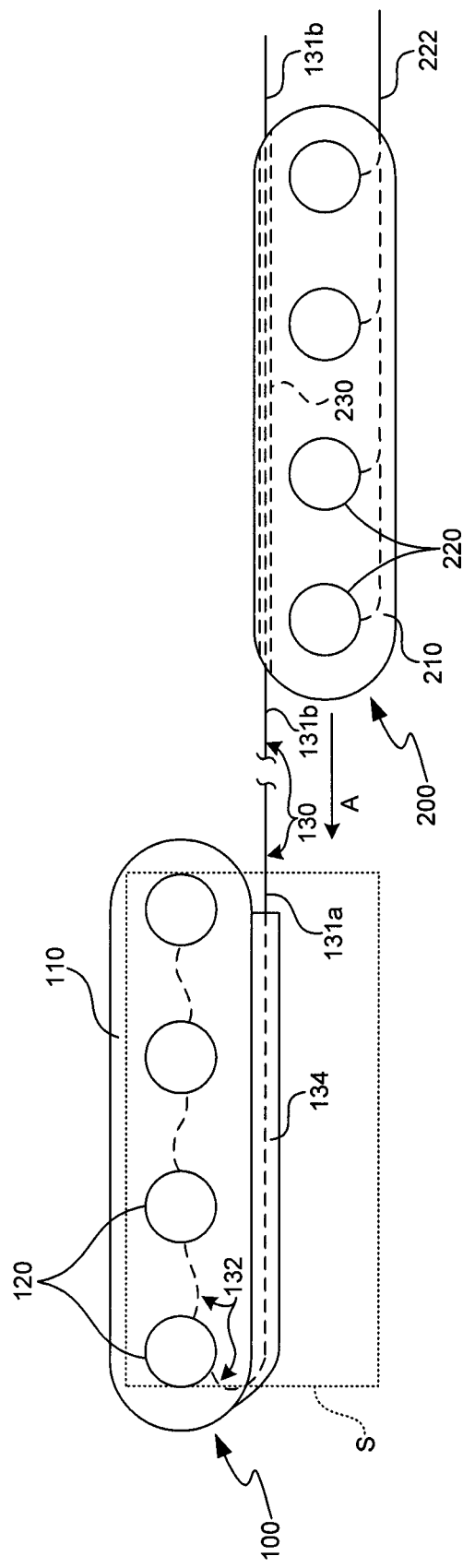
FIG. 4 is a bottom plan view of a first electrode unit and a second electrode unit of an electrode assembly in accordance with another embodiment of the invention.

FIG. 4 illustrates an alternative embodiment of the first electrode unit 100, and like reference numbers refer to like components in FIGS. 3A and 4. The embodiment of the first electrode unit 100 illustrated in FIG. 4 is different than the embodiment illustrated in FIG. 3A in that the guideline 130 is also the electrical line that provides the current to the first electrodes 120. For example, the guideline 130 of the embodiment shown in FIG. 4 can be an electrically conductive material in which the end 132 extends through the support 110 and electrically contacts the first electrodes 120.

Figure 5A:
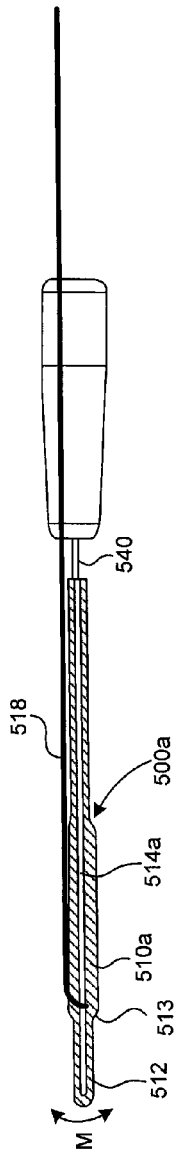
FIGS. 5A-5C are cross-sectional views of stages of assembling an electrode assembly within a patient in accordance of an embodiment of a method of the invention.

FIGS. 5A-5D illustrate various aspects of a first electrode unit 500a and a second electrode unit 500b in accordance with another embodiment. Referring to FIG. 5A, the first electrode unit 500a includes a first support 510a having a flexible tip 512 and a first channel 514a. The first electrode unit 500a further includes a guideline 518 having a distal section attached to the first support 510a and a proximal section extending proximally from the distal section. In operation, a flexible wire stylet 540 is inserted in the channel 514a and pushed against the distal tip 512 to drive the first electrode unit 500a through a needle and into the patient until the first electrode unit 500a is positioned at the stimulation site. The distal end of the stylet 540 can be bent to change the direction of the distal tip 512 (as shown by arrow M) for steering the first electrode unit 500a through the patient. In one example, the first support 510a has a non-circular cross-sectional shape in the region of the first electrodes 520a (best shown in FIG. 5D), the distal tip 512 is flexible and has a circular cross-sectional shape, and the first electrode unit 500a has a transition portion 513 transitioning from the non-circular cross-section of the first support 510a to the circular cross-section of the distal tip 512. The non-circular cross-section of the first support 510a can be oval, elliptical or another shape that provides a lower-wider profile than a circle. After the first electrode unit 500a is positioned percutaneously at a desired stimulation site, the stylet 540 is removed from the first electrode unit 500a.

Figure 5B:
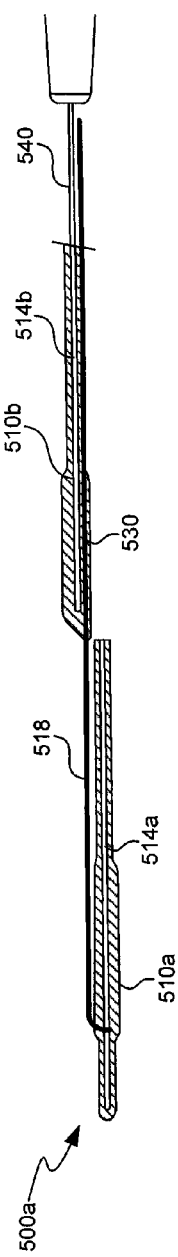
Figure 5C:
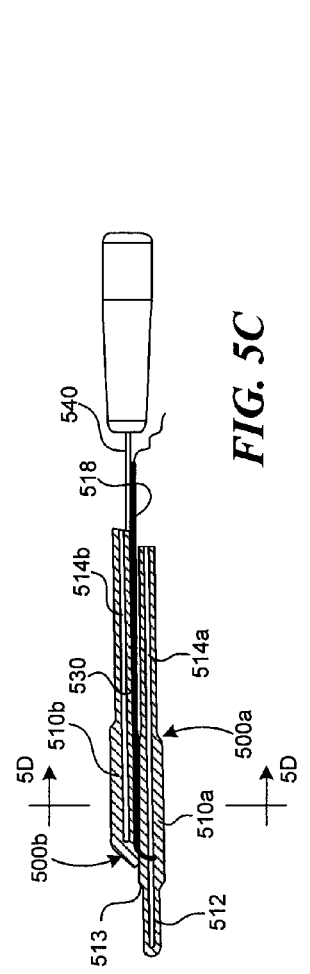
Figure 5D:
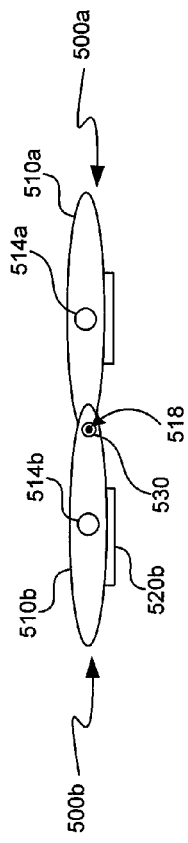
FIG. 5D is a cross-sectional view taken along line 5D-5D of FIG. 5C illustrating an assembled electrode assembly in accordance with an embodiment of the invention.

FIG. 5B illustrates an embodiment of the interaction between the first electrode unit 500a and the second electrode unit 500b. The second electrode unit 500b can include a second support 510b, a second channel 514b, and a lumen 530. In operation, the stylet 540 is placed into the second channel 514b and the proximal end of the guideline 518 is positioned in the lumen 530. An operator pushes the stylet 540 distally to slide the second electrode unit 500b over the guideline 518 via the interface between the guideline 518 and the lumen 530. Referring to FIG. 5C, the second electrode unit 500b is advanced distally until the second electrode unit 500b is adjacent to the first electrode unit 500a. Referring to FIG. 5D, the paddle portions of the first and second electrode units 500a and 500b can be positioned in a side-by-side relationship in which first electrodes 520a on the first electrode unit 500a and second electrodes 520b on the second electrode unit 500b face in a common direction and are electrically isolated from the back side surfaces of the first and second electrode units 500a and 500b, respectively. Additionally, the interface between the guideline 518 and the lumen 530 effectively engages or otherwise interlocks the first and second electrode units 500a-b together.

FIG. 6 is a cross-sectional view of another embodiment of an assembled electrode assembly 600 having a first electrode unit 601 and a second electrode unit 602. The first electrode unit 601 includes a first support 610a having a paddle portion, at least one first electrode 620a at the first support 610a, and a first connector 630a at a side of the first support 610a. The first electrode unit 601 can further include a first channel 611a extending through the first support 610a to receive a stylet or guidewire. The first electrode unit 601 can also include a guideline 640 similar to the guideline 130 described above with reference to FIG. 1A. The second electrode unit 602 can include a second support 610b, at least one second electrode 620b carried by the second support 610b, a second lumen 611b through the second support 610b to receive a guidewire or stylet, and a second connector 630b having a lumen 650. In this embodiment, the first and second connectors 630a-b are oppositely charged magnets that attract each other. In operation, therefore, the guideline 640 of the first electrode unit 601 passes through the lumen 650 of the second electrode unit 602 as the second electrode unit 602 advances distally until the first and second connectors 630a-b are adjacent to each other. The first and second connectors 630a-b then attract each other to secure the first and second electrode units 601 and 602 in a side-by-side relationship.

FIG. 7 illustrates an implantable electrode assembly 700 in accordance with yet another embodiment having a first electrode unit 701 and a second electrode unit 702. The first electrode unit 701 can have a first support 710a, and the second electrode unit 702 can have a second support 710b. The first and second electrode units 701 and 702 can accordingly have one or more electrodes first 720a and second electrodes 720b, respectively. The first electrode unit 701 further includes a first lumen 711a for receiving a stylet or guidewire, and the second electrode unit 702 can similarly have a second lumen 711b. The first and second electrode units 701 and 702 can be coupled together with a tongue and groove assembly. For example, the first electrode unit 701 can have a first connector 730a with a longitudinal opening and a larger longitudinal internal cavity. The first electrode unit 701 can also have a guideline 740 that runs longitudinally through the internal cavity of the first connector 730a. The second electrode unit 702 can have a second connector 730b having a neck 731 configured to fit in the opening of the first connector 730a and a bulbous portion 732 configured to be received in the internal cavity of the first connector 730a. The bulbous portion 732 of the second connector 730b is larger than the opening of the first connector 730a to restrict lateral movement between the first and second electrode units 701 and 702. The second connector 730b further includes a lumen 750 that receives the guideline 740. In operation, the bulbous portion of the second connector 730b slides longitudinally within the larger internal cavity of the first connector 730a as the lumen 750 advances over the guideline 740.

Figure 8:
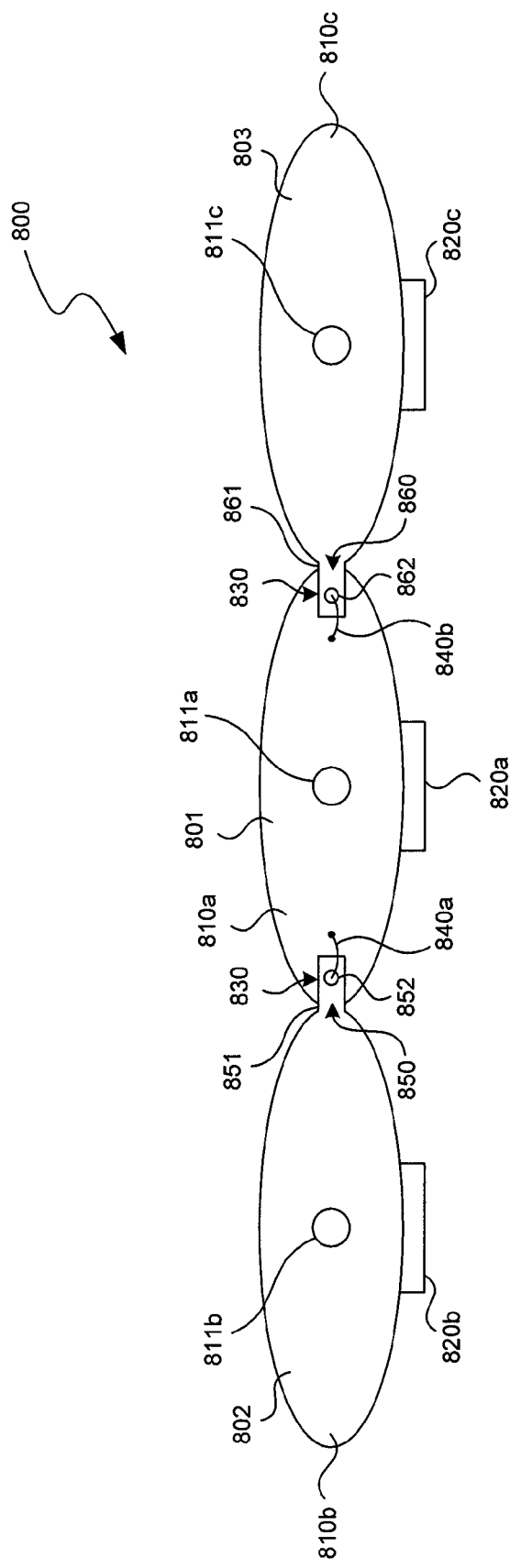
FIG. 8 is a cross-sectional view of an assembled electrode assembly in accordance with still another embodiment of the invention.

FIG. 8 illustrates an embodiment of another electrode assembly 800 having a first electrode unit 801, a second electrode unit 802, and a third electrode unit 803. The first electrode unit 801 has a first support 810a with a first channel 811a to receive a guidewire or stylet, at least one first electrode 820a carried by the first support 810a, and grooves 830 on each side of the first support 810a that define separate connectors. The first electrode unit 801 can further include a first guideline 840a at one side of the first support 810a and a second guideline 840b at the other side of the first support 810a. The second electrode unit 802 and the third electrode unit 803 can be mirror images of each other, or in other embodiments they can have different configurations. The second electrode unit 802 can accordingly include a second support 810b with a second channel 811b, at least one second electrode 820b carried by the second support 810b, and a second connector 850. The second connector 850 has a tongue 851 configured to fit into the groove 830 and a lumen 852 extending through the tongue 851. The third electrode unit 803 can include a third support 810c having a third channel 811c, at least one third electrode 820c carried by the third support 810c, and a third connector 860. The third connector 860 also has a tongue 861 and a lumen 862 extending through the tongue 861. In operation, the first guideline 840a is received in the lumen 852 of the second electrode unit 802 and the second guideline 840b is received in the lumen 862 of the third electrode unit 803. In one embodiment, the first and second electrode units 802 and 803 are advanced sequentially along the first and second guidelines 840a and 840b through the same percutaneous hole used to implant the first electrode unit 801 into the patient. The electrode assembly 800 accordingly includes three independently operable electrode units that are passed through one small percutaneous hole and assembled in vivo to cover an area having a cross-section that is much larger than the percutaneous entry hole. The electrode assembly 800 can accordingly provide monopolar, bi-polar, or tri-polar electrical fields to the neural tissue, muscle tissue, or other type of tissue subject to the electrical stimulation.

Figure 9A:
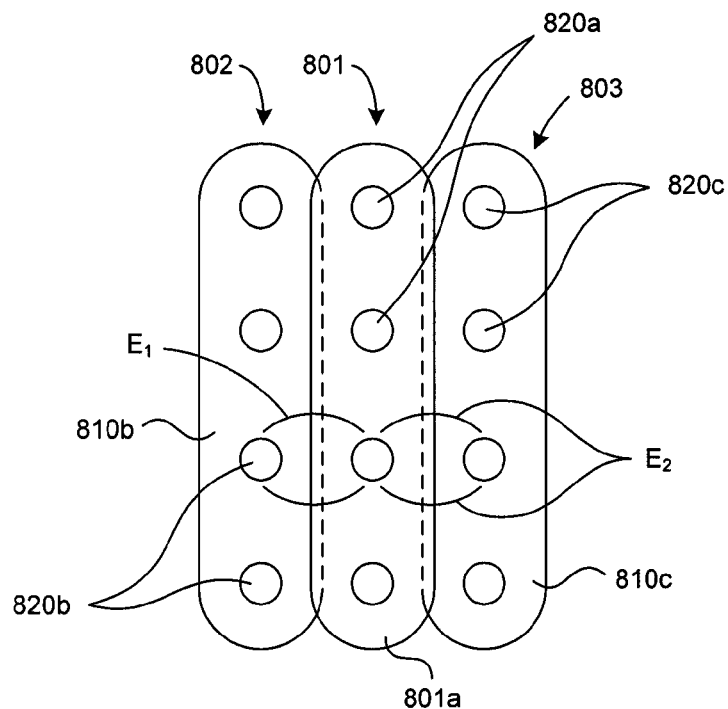
FIGS. 9A and 9B are bottom plan views of embodiments of assembled electrode assemblies in accordance with embodiments of the invention.
Figure 9B:
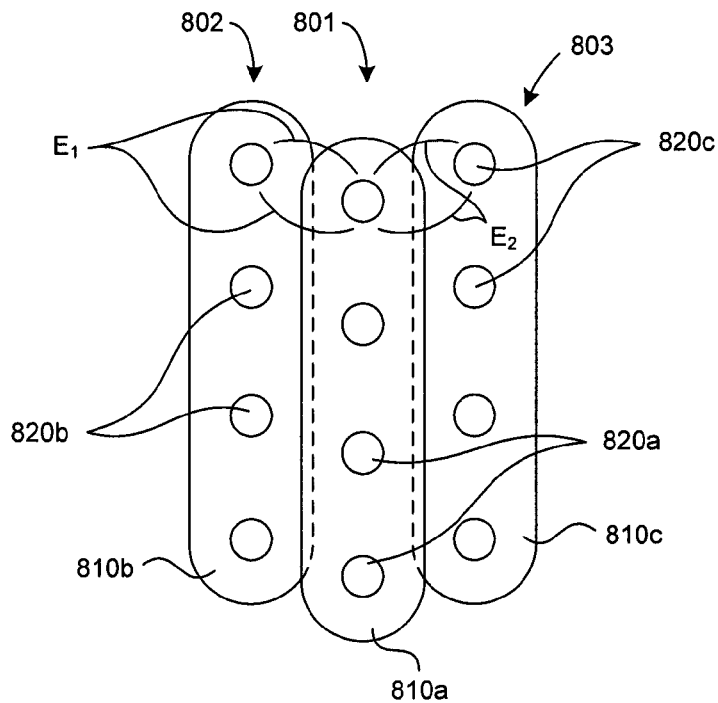

FIGS. 9A and 9B illustrate different orientations of the embodiment of the electrode assembly 800 illustrated in FIG. 8. Referring to FIG. 9A, the electrode units 801-803 can be arranged such that the first electrodes 820a are aligned with either or both of the second electrodes 820b and the third electrodes 820c. Such a configuration creates aligned electrical fields $E_1$ and $E_2$. The vectors of the electrical fields $E_1$ and $E_2$ can advantageously provide channel vectors oriented in directions generally followed by the neural structures. FIG. 9B illustrates an alternative orientation in which the first electrode unit 801 is staggered relative to the second and third electrode units 802 and 803 such that the first and second electrical fields $E_1$ and $E_2$ are at an acute angle relative to a medial superior-inferior axis of the spinal cord. The particular orientation between the first-third electrode units 801-803 can be configured to provide channel vectors in directions that generally follow the dorsal routes leaving the dorsal column at the intervertebral foramen of the spinal cord. Proximal to the brain, the dorsal root branches from the spinal column at a generally orthogonal orientation relative to the dorsal column. Distal of the brain, however, the dorsal roots branch from the dorsal column at increasingly inferior angles with respect to the dorsal column such that the degree to which the electrode units 801-803 can be staggered relative to each other may be particularly suitable for applications distal of the brain.

Figure 10:
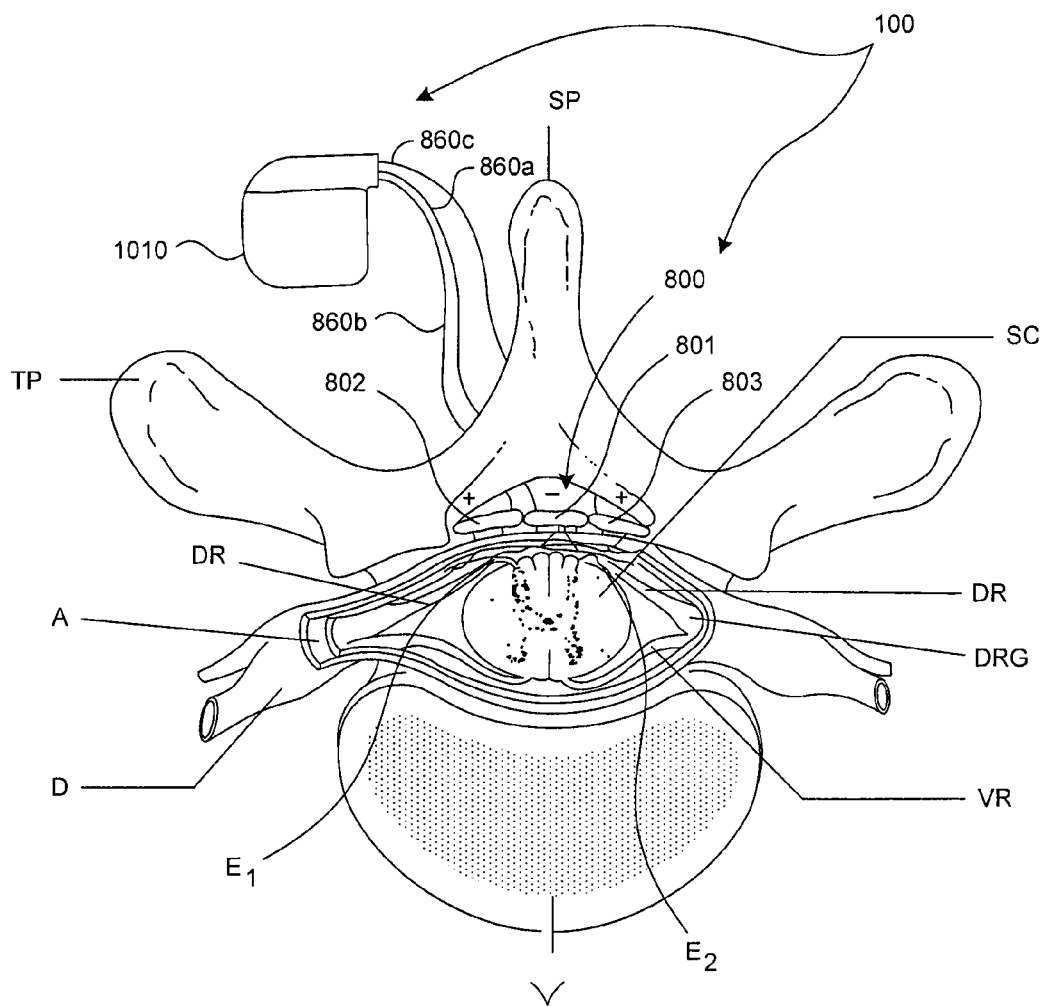
FIG. 10 is a cross-sectional view of a dorsal root spinal cord stimulation application using an electrode assembly in accordance with an embodiment of the invention.

FIG. 10 is a cross-sectional view that illustrates the relationship between the spinal cord, spinal nerves, vertebral column, and an embodiment of a stimulation system 1000 including an implantable pulse generator 1010 and an embodiment of the electrode assembly 800. To better understand this particular application, the illustrated anatomy will initially be described. The anatomy includes a spinal cord SC, dorsal roots of the spinal nerve DR, ventral roots of the spinal nerve VR, and a dorsal root ganglion DRG. The spinal cord SC, dorsal roots DR, and ventral roots VR are surrounded by arachnoid mater A, which is surrounded by dura mater D. The neural tissues are protected by a vertebral body V with transverse processes TP and a spinal process SP. In this particular application, the electrode assembly 800 is implanted by percutaneously implanting the first electrode unit 801 so that it is generally aligned with a posterior-anterior medial axis. The second electrode unit 802 is then implanted through the same hole as the first electrode unit 801 on one side of the first electrode unit 801, and then the third electrode unit 803 is implanted via the same hole on the other side of the first electrode unit 801. The second and third electrode units 802 and 803 can be implanted and engaged with the first electrode unit 801 as described above with reference to FIG. 8. The implantable pulse generator 1010 is implanted at a suitable location, and electrical lines 860a-c from the electrode units 801-803 are coupled to the pulse generator 1010. The implantable pulse generator 1010 can have hardware and/or software containing instructions that cause the pulse generator to provide the desired electrical signals to the patient. Suitable implantable pulse generators, locations for implanting the electrode assembly, and stimulation pulses for dorsal root stimulation are described in U.S. Provisional Patent Application No. 60/985,353 filed on Nov. 5, 2007.

In one embodiment of tri-polar stimulation, the electrodes of the first electrode unit 801 can be cathodes and the electrodes of the second and third electrode units 802 and 803 can be anodes to create the separate electrical fields $E_1$ and $E_2$ that affect the dorsal roots DR. The implantable pulse generator 1010 can accordingly include instructions that generate such tri-polar electrical fields. One aspect of the tri-polar embodiment illustrated in FIG. 10 is that the cathodic first electrodes of the first electrode unit 801 depolarize the nerves at the posterior-anterior medial axis where action potentials tend to fire while the anodic second and third electrodes hyperpolarize the nerves along the dorsal roots which decreases the intrinsic threshold and reduces firing of the nerves along the dorsal roots. The embodiment of the electrode assembly 800 shown in FIG. 10 can be implemented to establish an electrical nerve block without a painful or uncomfortable period before the nerves are blocked.

Several embodiments of the electrode assemblies described above provide the benefits of a large paddle-type array with the advantages of percutaneous implantation through a single, small percutaneous entry hole. By sequentially implanting each individual electrode unit and then assembling the electrode units in vivo, the electrode assemblies can use a single percutaneous entry hole and then be assembled to cover a large stimulation area. This is particularly well suited for dorsal root SCS because the large electrode arrays can provide more efficacy for pain relief and the percutaneous implantation reduces discomfort and complications for the patient. Several embodiments of the electrode assemblies also provide beneficial long-term features for SCS. For example, the relatively flat paddle portions of the electrode units do not tend to migrate, and this is particular so when several electrode units are assembled as described above with reference to FIGS. 3A-10. Moreover, several embodiments of the electrode assemblies conserve power and provide more control over the electrical fields because the electrodes face in a common direction toward the target neural tissue that is desirably subject to stimulation, but the back surfaces of the electrode arrays are electrically insolated from the electrodes such that energy is not wasted on non-target tissue and collateral stimulation is mitigated.

From the foregoing, it will be appreciated that specific embodiments of the foregoing disclosure have been described for purposes of illustration, but well-known structures and functions have not been shown or described in detail to avoid unnecessarily obscuring the description of the embodiments described above. Where the context permits, singular or plural terms may include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of features are not precluded. The foregoing embodiments can also be combined with each other to create more embodiments. For example, the casing 134 of the first electrode unit 100 or any of the connectors of the other electrode units can be used with the electrode assembly 800, or any of the first electrode units can have guidewire channels for over-the-wire implantation of the first electrode units. Therefore, the invention is not limited except as by the appended claims.

We claim:

1. An implantable neural stimulation electrode assembly, comprising:
    a first electrode unit having a dielectric first paddle, a plurality of first electrodes carried by the first paddle, and a guideline having a distal section fixed to the first paddle and a proximal section having a length configured to extend beyond the first paddle and externally of a patient when the first paddle is positioned within the patient, wherein the first paddle includes a first cross-sectional dimension, and wherein the guideline includes a second cross-sectional dimension, less than the first cross-sectional dimension; and
    a second electrode unit having a dielectric second paddle and a plurality of second electrodes carried by the second paddle, wherein the second paddle is configured to travel along the guideline from a first position spaced apart from the first paddle to a second position adjacent to and engaged with the first paddle in a side-by-side configuration within the patient.

2. The electrode assembly of claim 1 wherein the first electrode unit further comprises a deformable casing projecting from a side of the first paddle, and wherein a portion of the distal section of the guideline is encased within the casing.

3. The electrode assembly of claim 2 wherein the casing is configured to split apart as the second paddle advances distally adjacent to the first paddle.

4. The electrode assembly of claim 1 wherein the second electrode unit further comprises a lumen configured to receive and slide over the guideline until the second paddle is adjacent the first paddle.

5. The electrode assembly of claim 4 wherein the first electrode unit further comprises a first connector and the second electrode unit further comprises a second connector, and wherein the first and second connectors are configured to engage each other when the second paddle is adjacent the first paddle.

6. The electrode assembly of claim 5 wherein the first connector comprises a first magnet and the second connector comprises a second magnet.

7. The electrode assembly of claim 5 wherein:
    the first connector comprises a longitudinal opening along a side of the first paddle and a longitudinal cavity within the first paddle that is exposed to the longitudinal opening, and wherein the guideline extends longitudinally through the longitudinal cavity; and
    the second connector comprises a neck projecting from a side of the second paddle and a bulbous portion projecting from the neck, and wherein the lumen of the second electrode unit extends longitudinally through the bulbous portion.

8. The electrode assembly of claim 4, further comprising an electrical line connected to at least one of the first electrodes, and wherein the electrical line is positioned to be external to the lumen.

9. The electrode assembly of claim 1 wherein:
    the first paddle comprises a first edge and a second edge, the guideline comprises a first guideline attached to the first paddle at the first edge and extending along the first edge, and the first electrode unit further comprises a first primary connector along the first edge, a second primary connector along the second edge, and a second guideline attached to the first paddle at the second edge and extending along the second edge;
    the second electrode unit comprises a lumen through the second paddle configured to receive the first guideline and a first secondary connector configured to engage the first primary connector such that the second paddle is adjacent to the first edge of the first paddle when implanted in a patient; and the electrode assembly further comprises a third electrode unit having a dielectric third paddle, a plurality of third electrodes carried by the third paddle, a lumen through the third paddle configured to receive the second guideline, and a second secondary connector configured to engage the second primary connector such that the third paddle is adjacent to the second edge of the first paddle when implanted in a patient.

10. The electrode assembly of claim 9 wherein the first electrodes are cathodes and the second and third electrodes are anodes.

11. The electrode assembly of claim 1 wherein the distal section of the guideline is coupled to the first electrodes, the guideline is composed of an electrically conductive material, and the proximal section of the guideline has an electrical terminal configured to engage a pulse generator.

12. The electrode assembly of claim 1 wherein the first electrode unit further comprises a first channel configured to receive a stylet and/or a guidewire, the second electrode unit further comprises a lumen configured to receive and slide over the guideline, and the second electrode unit also comprises a second channel configured to receive the stylet and/or a guidewire.

13. The electrode assembly of claim 12 wherein the first electrode unit further comprises a flexible tip projecting distally from the first paddle and the first channel extends into the flexible tip.

14. The electrode assembly of claim 1, further comprising an electrical line connected to at least one of the first electrodes, and wherein the guideline is distinct from the electrical line.

* * * * *